(12) United States Patent  
Moturu et al.

(10) Patent No.: US 11,908,585 B2  
(45) Date of Patent: Feb. 20, 2024

(54) METHOD FOR MODELING BEHAVIOR AND DEPRESSION STATE

(71) Applicant: OrangeDot, Inc., Santa Monica, CA (US)

(72) Inventors: Sai Moturu, San Francisco, CA (US); Anmol Madan, San Francisco, CA (US); Shishir Dash, San Francisco, CA (US); Karim Wahba, San Francisco, CA (US); Gourab De, San Francisco, CA (US)

(73) Assignee: OrangeDot, Inc., Santa Monica, CA (US)

( * ) Notice: Subject to any disclaimer, the term of this patent is extended or adjusted under 35 U.S.C. 154(b) by 0 days.

(21) Appl. No.: 17/517,561

(22) Filed: Nov. 2, 2021

(65) Prior Publication Data

US 2022/0059235 A1 Feb. 24, 2022

Related U.S. Application Data

(63) Continuation of application No. 16/056,984, filed on Aug. 7, 2018, now Pat. No. 11,195,625, which is a (Continued)

(51) Int. Cl.
*G16H 50/50* (2018.01)
*G16H 10/20* (2018.01)
(Continued)

(52) U.S. Cl.
CPC .............. *G16H 50/50* (2018.01); *G16H 10/20* (2018.01); *G16H 40/63* (2018.01); *G16H 40/67* (2018.01);
(Continued)

(58) Field of Classification Search
CPC ........ G16H 50/50; G16H 40/67; G16H 40/63; G16H 10/20; G16H 20/10; G16H 20/70; G16Z 99/00
(Continued)

(56) References Cited

U.S. PATENT DOCUMENTS 4,845,323 A 7/1989 Beggs
6,356,940 B1 3/2002 Short
(Continued)

FOREIGN PATENT DOCUMENTS

CN 101600008 A 12/2009
DE 102016101665 A1 8/2016
(Continued)

OTHER PUBLICATIONS

Calvo, et al., "Natural language processing in mental health applications using non-clinical texts", Natural Language Engineering 23 (5): 649-685. © Cambridge University Press 2017. (Year: 2017).
(Continued)

*Primary Examiner* — Michael Tomaszewski
(74) *Attorney, Agent, or Firm* — Jeffrey Schox; Caitlin Ploch

(57) ABSTRACT

A method and system for modeling behavior and depression state of an individual, the method comprising: receiving a log of use dataset associated with communication behavior of the individual during a time period; receiving a supplementary dataset characterizing activity of the individual during the time period; receiving a survey dataset including responses, to at least one of a set of depression-assessment surveys, associated with a set of time points of the time period; generating a predictive analysis of a depression-risk state of the individual associated with at least a portion of the time period, from at least one of the log of use dataset, the
(Continued)

supplementary dataset, and the survey dataset; and generating an alert upon detection that a set of parameters from the predictive analysis of the depression-risk state satisfy a threshold condition.

18 Claims, 6 Drawing Sheets

Related U.S. Application Data continuation of application No. 14/839,053, filed on Aug. 28, 2015, now Pat. No. 10,068,670, which is a continuation-in-part of application No. 13/969,339, filed on Aug. 16, 2013, now abandoned.

(60) Provisional application No. 61/683,867, filed on Aug. 16, 2012, provisional application No. 61/683,869, filed on Aug. 16, 2012, provisional application No. 62/043,201, filed on Aug. 28, 2014, provisional application No. 62/069,177, filed on Oct. 27, 2014, provisional application No. 62/043,328, filed on Aug. 28, 2014, provisional application No. 62/043,566, filed on Aug. 29, 2014.

(51) Int. Cl.
*G16Z 99/00* (2019.01)
*G16H 40/67* (2018.01)
*G16H 40/63* (2018.01)
*G16H 20/70* (2018.01)
*G16H 20/10* (2018.01)

(52) U.S. Cl.
CPC ............ *G16Z 99/00* (2019.02); *G16H 20/10* (2018.01); *G16H 20/70* (2018.01)

(58) Field of Classification Search
USPC .............................................. 705/2–3; 703/6
See application file for complete search history.

(56) References Cited

U.S. PATENT DOCUMENTS

| | | | |
|---|---|---|---|
| 6,827,670 B1 | 12/2004 | Stark et al. | |
| 7,188,151 B2 | 3/2007 | Kumar et al. | |
| 7,246,677 B2 | 7/2007 | Fredriksson et al. | |
| 7,248,677 B2 | 7/2007 | Randall et al. | |
| 7,337,158 B2 | 2/2008 | Fratkina et al. | |
| 7,376,700 B1 | 5/2008 | Clark et al. | |
| 7,395,216 B2 | 7/2008 | Rosenfeld et al. | |
| 7,584,166 B2 | 9/2009 | Grichnik | |
| 7,761,309 B2 | 7/2010 | Sacco et al. | |
| 7,818,185 B2 | 10/2010 | Bjorner et al. | |
| 7,912,528 B2 | 3/2011 | Krishnan et al. | |
| 7,914,468 B2 | 3/2011 | Shalon et al. | |
| 8,160,901 B2 | 4/2012 | Heywood et al. | |
| 8,265,955 B2 | 9/2012 | Michelson et al. | |
| 8,398,538 B2 | 3/2013 | Dothie et al. | |
| 8,423,387 B1 | 4/2013 | Mirza | |
| 8,488,761 B2 | 7/2013 | Reding et al. | |
| 8,500,635 B2 | 8/2013 | Zilca et al. | |
| 8,622,900 B2 | 1/2014 | Jain et al. | |
| 8,655,817 B2 | 2/2014 | Hasey et al. | |
| 8,684,922 B2 | 4/2014 | Tran | |
| 8,726,195 B2 | 5/2014 | Bill | |
| 8,781,102 B2 | 7/2014 | Conway et al. | |
| 8,977,248 B1 | 3/2015 | Bladon et al. | |
| 9,019,106 B2 | 4/2015 | Alameh et al. | |
| 9,116,669 B2 | 8/2015 | Desai et al. | |
| 9,195,948 B2 | 11/2015 | Son et al. | |
| 9,286,442 B2 | 3/2016 | Csoma et al. | |
| 9,294,403 B2 | 3/2016 | Mejia et al. | |
| 9,497,585 B1 | 11/2016 | Cooley et al. | |
| 9,684,922 B2 | 6/2017 | Elberbaum | |
| 9,713,724 B2 | 7/2017 | Petersen et al. | |
| 9,754,220 B1 | 9/2017 | Brestoff et al. | |
| 9,763,592 B2 | 9/2017 | Le et al. | |
| 11,710,576 B2 | 7/2023 | Shah | |
| 2002/0198473 A1 | 12/2002 | Kumar et al. | |
| 2003/0119794 A1 | 6/2003 | Bacaner et al. | |
| 2004/0078223 A1 | 4/2004 | Sacco et al. | |
| 2004/0122702 A1 | 6/2004 | Sabol et al. | |
| 2004/0122703 A1 | 6/2004 | Walker et al. | |
| 2004/0143453 A1 | 7/2004 | Weaver | |
| 2004/0199401 A1 | 10/2004 | Wagner et al. | |
| 2004/0225340 A1 | 11/2004 | Evans | |
| 2005/0020903 A1 | 1/2005 | Krishnan et al. | |
| 2005/0055321 A1 | 3/2005 | Fratkina et al. | |
| 2005/0069936 A1 | 3/2005 | Diamond et al. | |
| 2005/0108051 A1 | 5/2005 | Weinstein | |
| 2005/0169446 A1 | 8/2005 | Randall et al. | |
| 2006/0064037 A1 | 3/2006 | Shalon et al. | |
| 2007/0022612 A1 | 2/2007 | Perrin | |
| 2007/0094048 A1* | 4/2007 | Grichnik | G16H 50/20 705/2 |
| 2007/0226012 A1 | 9/2007 | Salgado et al. | |
| 2007/0288266 A1 | 12/2007 | Sysko et al. | |
| 2008/0059570 A1 | 3/2008 | Bill | |
| 2008/0061125 A1 | 3/2008 | Langlois et al. | |
| 2008/0201429 A1 | 8/2008 | Barbell et al. | |
| 2009/0125333 A1 | 5/2009 | Heywood et al. | |
| 2009/0161907 A1 | 6/2009 | Healey et al. | |
| 2009/0254971 A1 | 10/2009 | Herz et al. | |
| 2010/0082367 A1 | 4/2010 | Hains et al. | |
| 2010/0179833 A1 | 7/2010 | Roizen et al. | |
| 2010/0198614 A1 | 8/2010 | Chopra et al. | |
| 2010/0203876 A1 | 8/2010 | Krishnaswamy | |
| 2010/0280838 A1 | 11/2010 | Bosworth et al. | |
| 2010/0325588 A1 | 12/2010 | Reddy et al. | |
| 2011/0009715 A1 | 1/2011 | O et al. | |
| 2011/0015467 A1 | 1/2011 | Dothie et al. | |
| 2011/0066036 A1 | 3/2011 | Zilca et al. | |
| 2011/0082712 A1 | 4/2011 | Eberhardt et al. | |
| 2011/0118555 A1* | 5/2011 | Dhumne | A61M 21/02 600/300 |
| 2011/0119212 A1 | 5/2011 | De et al. | |
| 2011/0125238 A1 | 5/2011 | Nofzinger | |
| 2011/0161110 A1 | 6/2011 | Mault | |
| 2011/0184250 A1 | 7/2011 | Schmidt et al. | |
| 2011/0245633 A1 | 10/2011 | Goldberg et al. | |
| 2011/0295621 A1 | 12/2011 | Farooq et al. | |
| 2011/0306028 A1 | 12/2011 | Galimore | |
| 2011/0314558 A1 | 12/2011 | Song et al. | |
| 2012/0016218 A1 | 1/2012 | Lau et al. | |
| 2012/0053425 A1 | 3/2012 | Michelson et al. | |
| 2012/0131183 A1 | 5/2012 | Heidt et al. | |
| 2012/0143013 A1 | 6/2012 | Davis et al. | |
| 2012/0179480 A1 | 7/2012 | Patel et al. | |
| 2012/0203545 A1 | 8/2012 | Shaw | |
| 2012/0221357 A1 | 8/2012 | Krause et al. | |
| 2012/0289791 A1 | 11/2012 | Jain et al. | |
| 2013/0004129 A1 | 1/2013 | Zhang | |
| 2013/0041290 A1 | 2/2013 | Kording et al. | |
| 2013/0042116 A1 | 2/2013 | Sakumoto | |
| 2013/0085758 A1 | 4/2013 | Csoma et al. | |
| 2013/0085773 A1 | 4/2013 | Yao et al. | |
| 2013/0095459 A1 | 4/2013 | Tran | |
| 2013/0117040 A1 | 5/2013 | James et al. | |
| 2013/0154838 A1 | 6/2013 | Alameh et al. | |
| 2013/0179178 A1 | 7/2013 | Vemireddy et al. | |
| 2013/0246330 A1 | 9/2013 | Son et al. | |
| 2013/0297536 A1* | 11/2013 | Almosni | G16H 50/20 706/12 |
| 2013/0324861 A1 | 12/2013 | Ando et al. | |
| 2014/0019161 A1 | 1/2014 | Op Den Buijs et al. | |
| 2014/0039907 A1 | 2/2014 | Schaefer et al. | |
| 2014/0039914 A1 | 2/2014 | Dansereau et al. | |
| 2014/0052465 A1 | 2/2014 | Madan et al. | |
| 2014/0052474 A1 | 2/2014 | Madan et al. | |
| 2014/0257439 A1 | 9/2014 | Douglas | |
| 2015/0003247 A1 | 1/2015 | Mejia et al. | |
| 2015/0187199 A1 | 7/2015 | Chang et al. | |

(56) References Cited

U.S. PATENT DOCUMENTS

| | | |
|---|---|---|
| 2015/0310606 A1 | 10/2015 | Shreve et al. |
| 2015/0370994 A1 | 12/2015 | Madan et al. |
| 2016/0292862 A1 | 10/2016 | Mask |
| 2016/0317781 A1 | 11/2016 | Proud |
| 2017/0124643 A1 | 5/2017 | Haimi et al. |
| 2018/0089449 A1 | 3/2018 | Boudreau et al. |
| 2018/0342326 A1 | 11/2018 | Moturu et al. |
| 2018/0374046 A1 | 12/2018 | Powers et al. |
| 2019/0042699 A1 | 2/2019 | Bastide et al. |
| 2020/0242566 A1 | 7/2020 | Agarwal et al. |
| 2021/0390625 A1 | 12/2021 | Hayes et al. |
| 2022/0061746 A1 | 3/2022 | Lyman et al. |

FOREIGN PATENT DOCUMENTS

| | | |
|---|---|---|
| JP | 2003339674 | 12/2003 |
| JP | 2010514497 A | 5/2010 |
| WO | 02067122 A1 | 8/2002 |
| WO | 2008085308 A1 | 7/2008 |
| WO | 2008096634 A1 | 8/2008 |
| WO | 2012025622 A2 | 3/2012 |
| WO | 2013042116 A1 | 3/2013 |
| WO | 2015003247 A1 | 1/2015 |

OTHER PUBLICATIONS

Coppersmith, et al., "Natural Language Processing of Social Media as Screening for Suicide Risk", Biomedical Informatics Insights vol. 10: 1-11 © The Author(s) 2018. (Year: 2018).

Ji, et al., "Supervised Learning for Suicidal Ideation Detection in Online User Content", Hindawi Complexity vol. 2018, Article ID 6157249, 10 pages https://doi.org/10.1155/2018/6157249. (Year: 2018).

Skaik, et al., "Using Social Media for Mental Health Surveillance: A Review", ACM Comput. Surv. 53, 6, Article 129 (Dec. 2020 ), 31 pages. https://doi.org/10.1145/3422824. (Year: 2020).

Major Virginia Smith; et al. Work Time Interference With Family, and Psychological Distress' 2002, Journal of Applied Psychology, vol. 87, No. 3, 427-436 (Year: 2002), Feb. 21, 2018 00:00:00.0.

"Pifzer, Patient Health Questionnaire (PH-9)", Pfizer Non-Patent Literature, 1999, pp. 1 and 2.

Thomee, Sara, et al., "Mobile phone use and stress, sleep disturbances, and symptoms of depression among young adults—a prospective short study", BMC Public Health, Biomed Central, London, GB, vol. 11, No. 1, Jan. 31, 2011, p. 66.

Yen, Cheng-Fang, et al., "Symptoms of problematic cellular phone use, functional impairment and its association with depression among adolescents in Southern Taiwan", Journal of Adolescence, Academic Press, Amsterdam, NL, vol. 32, No. 4, Aug. 1, 2009, pp. 863-873.

\* cited by examiner

METHOD FOR MODELING BEHAVIOR AND DEPRESSION STATE

CROSS-REFERENCE TO RELATED APPLICATIONS

This application is a continuation of U.S. application Ser. No. 16/056,984, filed 7 Aug. 2018, which is a continuation of U.S. application Ser. No. 14/839,053, filed 28 Aug. 2015, which is a continuation-in-part application of U.S. application Ser. No. 13/969,339 filed 16 Aug. 2013, which claims the benefit of U.S. Provisional Application Ser. No. 61/683,867 filed on 16 Aug. 2012 and U.S. Provisional Application Ser. No. 61/683,869 filed on 16 Aug. 2012, which are each incorporated in its entirety herein by this reference.

U.S. application Ser. No. 14/839,053, filed 28 Aug. 2015, claims the benefit of U.S. Provisional Application Ser. No. 62/043,201 filed 28 Aug. 2014, U.S. Provisional Application Ser. No. 62/069,177 filed 27 Oct. 2014, U.S. Provisional Application Ser. No. 62/043,328 filed 28 Aug. 2014, and U.S. Provisional Application Ser. No. 62/043,566 filed 29 Aug. 2014, which are each incorporated in its entirety herein by this reference.

TECHNICAL FIELD

This invention relates generally to the field of mental health and more specifically to a new and useful method for modeling behavior and states of depression and/or anxiety in the field of mental health.

BACKGROUND

Major depressive disorder (MDD) is characterized by a combination of symptoms that interfere with a person's ability to work, sleep, study, eat, and enjoy once-pleasurable activities. Major depression is typically disabling and prevents a person from functioning normally. Some patients with MDD may experience only a single episode within their lifetime, but more often, an individual/patient with MDD can have multiple episodes. Two diagnostic criteria for MDD are depressed mood and loss of interest or pleasure in most activities, at least one of which must occur for a duration of at least two weeks. Additional diagnostic symptoms, including dysphoric mood, appetite change, and thoughts of death are also common. Furthermore, depression is often comorbid with anxiety, which can also have a debilitating effect on individuals.

Unfortunately, current standards of detection, diagnosis and treatment of MDD, anxiety, and/or other depressive disorders, as well as social barriers to seeking diagnosis and treatment, are responsible for delays in diagnoses of disorders and/or misdiagnoses of disorders, which cause disorders to remain untreated. Furthermore, changes in depressive state often go undetected, resulting in regressions in depressive state, patient harm, or even death. While the delays can be due to the sensitive nature of such disorders, current standards of detection diagnosis are severely deficient in many controllable aspects. In addition to these deficiencies, further limitations in detection, diagnosis, treatment, and/or monitoring of patient progress during treatment prevent adequate care of patients with diagnosable and treatable depressive disorders.

As such, there is a need in the field of mental health for a new and useful method for modeling behavior and states of depression and/or anxiety. This invention creates such a new and useful method for modeling behavior and states of depression and/or anxiety.

DESCRIPTION OF THE EMBODIMENTS

The following description of the embodiments of the invention is not intended to limit the invention to these embodiments, but rather to enable any person skilled in the art to make and use this invention.

1. Method

Figure 1:
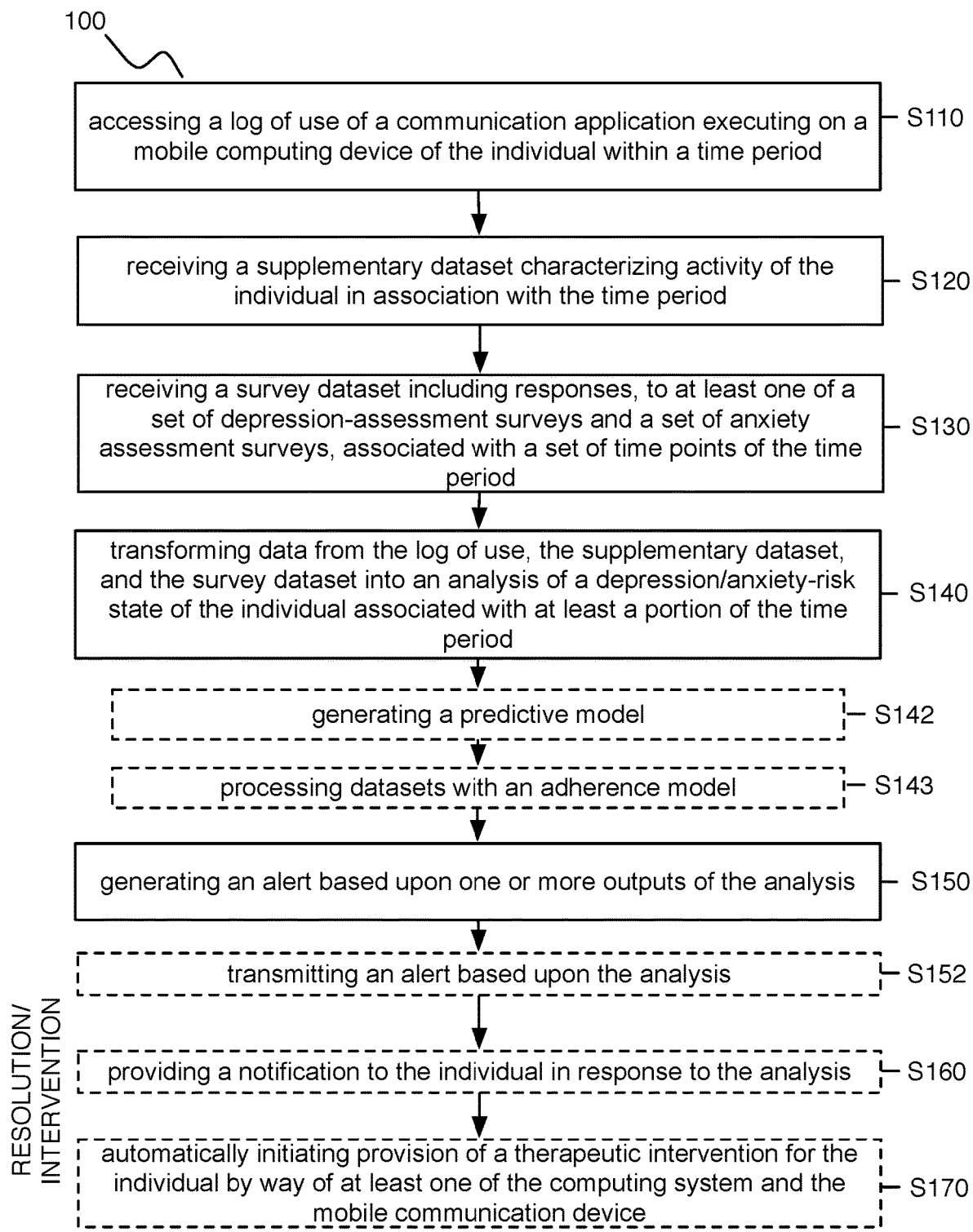
FIG. 1 is a flowchart of an embodiment of a method for modeling behavior and depression state.

As shown in FIG. 1, a method 100 for modeling behavior and depression state of an individual includes: accessing a log of use of a communication application executing on a mobile communication device of the individual within a time period S110; receiving a supplementary dataset characterizing activity of the individual in association with the time period S120; receiving a survey dataset including responses, to at least one of a set of depression-assessment surveys, associated with a set of time points of the time period, from the individual S130; for at least a time point of the set of time points, transforming data from the log of use, the supplementary dataset, and the survey dataset into an analysis of a depression-risk state of the individual associated with at least a portion of the time period S140; and generating an alert based upon one or more outputs of the analysis S150. In some variations, the method 100 can further include any one or more of: providing a notification to the individual, at the mobile communication device, in response to the analysis S160; and automatically initiating provision of a therapeutic intervention for the individual by way of at least one of the computing system and the mobile communication device S170.

The method 100 functions to analyze communication behavior and other information regarding an individual (e.g., patient, at-risk individual) exhibiting symptoms of depression, in order to assess risk of the individual in entering an adverse depressive state. As such, the method 100 can facilitate monitoring of states of depression in an individual exhibiting symptoms of depression, by enabling detection of changes in the individual's condition. In a specific application, the method 100 can monitor and analyze communication behavior, mobility behavior, and/or other behavior detected from any other suitable sensor(s) associated with an individual with depression over time, and provide an alert to a caretaker associated with the patient and/or to the patient upon detection that the individual has entered or is at risk of entering a critical state of depression (e.g., suicidal state). Thus, the method 100 can provide a predictive model for one or more individuals experiencing symptoms of MDD or other depressive disorders (e.g., perinatal depression, comorbid depression), as well as an intervention model for providing interventions at key time points, to optimize improvement in individual outcomes (e.g., as exhibited by an improved state). The intervention model can thus implement an anticipated patient depressive state to drive automated or manual targeted intervention for a patient (e.g., via a phone call, email, health tip notification, insight, other electronic communication, other electronic device-based messaging, other electronic device-based notifications, etc.) in some applications. In further embodiments, an analysis of the method 100 can be used to generate and/or provide therapeutic regimens to the patient as a therapeutic measure in promoting the psychological health of a patient with clinically-diagnosed depression.

In relation to perinatal depression, applications of the method 100 can provide therapeutic intervention to women experiencing depression during pregnancy (e.g., women in their third trimester of pregnancy) in relation to one or more of: depression, mood, pain, anxiety related to pregnancy, general anxiety, and any other adverse mental state adverse state associated with pregnancy. As such, in relation to perinatal depression, the method 100 can improve patient outcomes in terms of patient function, patient quality of life, and overall child development. In relation to depression and poor self-management associated with diabetes, applications of the method 100 can detect trends toward adverse health states and provide therapeutic intervention to patients with type II diabetes. Variations of the method 100 can, however, be applied to improve patient outcomes in relation to any other state or condition associated with depression.

In relation to anxiety, which can be comorbid with depression, applications of the method 100 can adapted to provide therapeutic intervention for individuals experiencing any suitable form of anxiety in the form of one or more of: generalized anxiety disorder (GAD), obsessive-compulsive disorder; panic disorder, post-traumatic stress disorder (PTSD), social anxiety disorder, phobias, and any other form or manifestation of anxiety. As such, in relation to anxiety, the method 100 can improve patient outcomes in terms of patient function and patient quality of life, in cooperation with or entirely independent of detection and treatment of depression in the individual (e.g., for individuals with one or both of depression and anxiety). Variations of the method 100 can, however, be applied to improve patient outcomes in relation to any other state or condition associated with depression, anxiety, or both depression and anxiety.

While the method 100 can be implemented for a single individual exhibiting symptoms of depression, the method 100 can additionally or alternatively be implemented for a population of individuals (e.g., including the individual, excluding the individual), wherein the population of individuals can include individuals similar to and/or dissimilar to the individual (e.g., in exhibition of symptoms of depression, in demographic group, in medical condition, etc.). Thus, information derived from the population of individuals can be used to provide additional insight into connections between the individual's behavior and risk of entering one of a spectrum of depressive states, due to aggregation of data from a population. In a specific example, the method 100 involves a population of patients between 18 and 65 years of age, each patient having a mobile communication device (e.g., smart phone, tablet, wearable computing device, etc.) and suffering from depression (e.g., as assessed from a score of 10 or greater on a PHQ-9 derived scale, as assessed from a score of 14 or greater on the HAM-D scale). In the specific example, the population of patients omits patients suffering from visual or hearing impairment, suicidal patients, pregnant women, new mothers (e.g., mothers who have given birth within the previous four months), and patients who have suffered a recent tragic event. However, variations of the specific example can alternatively include patients of any other suitable demographic or condition. For instance, pregnant women or new mothers can be included in variations of the method adapted for perinatal depression modeling, and patients suffering from other ailments can be included in variations of the method adapted for comorbid depression modeling.

The method 100 is preferably implemented at least in part by an embodiment of the system 200 described in Section 2 below, variations of which can be implemented at least in part by embodiments, variations, and examples of the system described in U.S. application Ser. No. 13/969,339 entitled "Method for Modeling Behavior and Health Changes" and filed on 16 Aug. 2013; however, the method 100 can alternatively be implemented using any other suitable system configured to process communication and/or other behavior of the patient, in aggregation with other information, in order to generate a model of behavior and depression state in the patient.

1.1 Method—Passive Data

Block S110 recites: accessing a log of use of a communication application (e.g., native communication application) executing on a mobile communication device by the patient within a time period, which functions to unobtrusively collect and/or retrieve communication-related data from a patient's mobile communication device. Preferably, Block S110 is implemented using a module of a processing subsystem configured to interface with a native data collection application executing on a mobile communication device (e.g., smartphone, tablet, personal data assistant (PDA), personal music player, vehicle, head-mounted wearable computing device, wrist-mounted wearable computing device, etc.) of the patient, in order to retrieve patient communication data. As such, in one variation, a native data collection application can be installed on the mobile communication device of the patient, can execute substantially continuously while the mobile communication device is in an active state (e.g., in use, in an on-state, in a sleep state, etc.), and can record communication parameters (e.g., communication times, durations, contact entities) of each inbound and/or outbound communication from the mobile communication device. In implementing Block S110, the mobile communication device can then upload this data to a database (e.g., remote server, cloud computing system, storage module), at a desired frequency (e.g., in near real-time, every hour, at the end of each day, etc.) to be accessed by the processing subsystem. In one example of Block S110, the native data collection application can launch on the patient's mobile communication device as a background process that gathers patient data once the patient logs into an account, wherein the patient data includes how and with what frequency the patient interacts with and communicates with other individuals through phone calls, e-mail, instant messaging, an online social network, etc.

As such, in accessing the log of use of the native communication application, Block S110, preferably enables collection of one or more of: phone call-related data (e.g., number of sent and/or received calls, call duration, call start and/or end time, location of patient before, during, and/or after a call, and number of and time points of missed or ignored calls); text messaging (e.g., SMS test messaging) data (e.g., number of messages sent and/or received, message length associated with a contact of the individual, message entry speed, delay between message completion time point and sending time point, message efficiency, message accuracy, time of sent and/or received messages, location of the patient when receiving and/or sending a message); data on textual messages sent through other communication venues (e.g., public and/or private textual messages sent to contacts of the patient through an online social networking system, reviews of products, services, or businesses through an online ranking and/or review service, status updates, "likes" of content provided through an online social networking system), vocal and textual content (e.g., text and/or voice data that can be used to derive features indicative of negative or positive sentiments) and any other suitable type of data.

Figure 2:
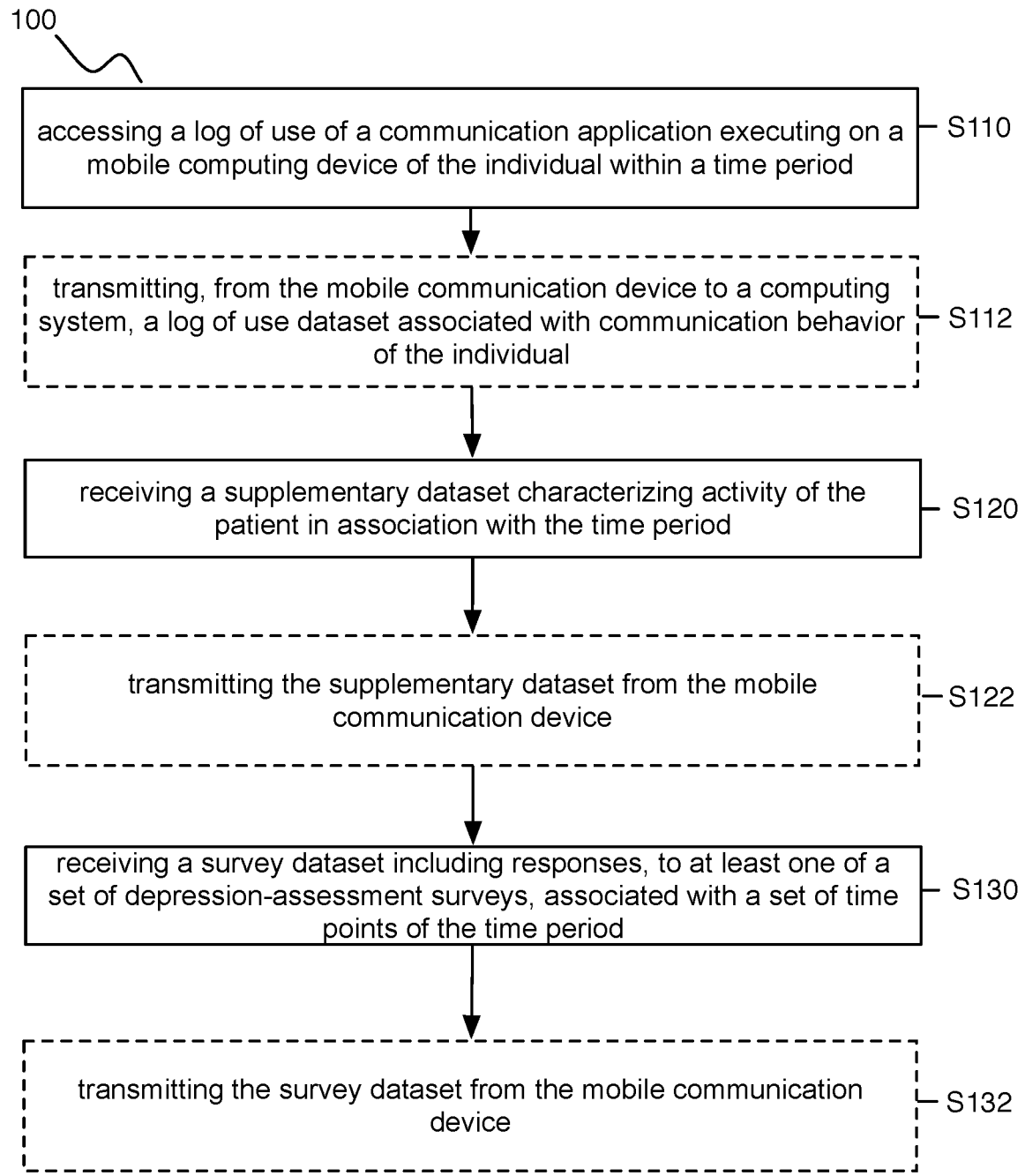
FIG. 2 is a flowchart of a variation of a portion of a method for modeling behavior and depression state.

In relation to accessing the log of communication, Block S110 can include accessing the log of use at the mobile communication device of the individual, and transmitting, from the mobile communication device to a computing system, a log of use dataset associated with communication behavior of the individual S112, as shown in FIG. 2. The computing system can be implemented in one or more of a processing module of the mobile communication device, a personal computer, a remote server, a cloud-based computing system, a computing module of any other suitable computing device (e.g., mobile computing device, wearable computing device, etc.), and any other suitable computing module. In transmitting the log of use dataset, a communication module (e.g., a hardware communication module associated with the communication application) can transmit data to the computing system by way of a wired and/or wireless data link (e.g., over Bluetooth, over Bluetooth LTE, etc.). However, Block S110 can include another other suitable variation of accessing the log of communication, transmitting data from the log of communication, and/or receiving a log of use dataset.

Block S120 recites: receiving a supplementary dataset characterizing activity of the individual in association with the time period, which functions to unobtrusively receive non-communication-related data from a patient's mobile communication device and/or other device configured to receive contextual data from the patient. Block S120 can include receiving non-communication-related data pertaining to the individual before, during, and/or after (or in the absence of) communication with another individual (e.g., a phone call) and/or computer network (e.g., a social networking application), as described above in relation to Block S110. Block S120 can include receiving one or more of: location information, movement information (e.g., related to physical isolation, related to lethargy), device usage information (e.g., screen usage information related to disturbed sleep, restlessness, and/or interest in mobile device activities), and any other suitable information. In variations, Block S120 or can include receiving location information of the individual by way of one or more of: receiving a GPS location of the individual (e.g., from a GPS sensor within the mobile communication device of the individual), estimating the location of the individual through triangulation of local cellular towers in communication with the mobile communication device, identifying a geo-located local Wi-Fi hotspot during a phone call, and in any other suitable manner. In applications, data received in Block S110 and S120 can be processed to track behavior characteristics of the individual, such as mobility, periods of isolation, quality of life (e.g., work-life balance based on time spent at specific locations), and any other location-derived behavior information.

As such, data from Blocks S110 and S120 can be merged in subsequent blocks of the method 100 to track the individual's mobility during a communication, for instance, in the analysis of Block S140. In variations, Block S120 can additionally or alternatively include receiving mobile usage data, including data indicative of screen unlocks and mobile application usage (e.g., by retrieving usage information from mobile operating system logs, by retrieving usage information from a task manager on a mobile communication device, etc.). Blocks S120 and/or S110 can therefore facilitate tracking of variations and periods of activity/inactivity for a patient through automatically collected data (e.g., from the patient's mobile communication device), in order to enable identification of periods of activity and inactivity by the individual (e.g., extended periods when the individual was hyperactive on the device or not asleep).

In additional variations, Block S120 can additionally or alternatively include receiving one or more of: physical activity- or physical action-related data (e.g., accelerometer data, gyroscope data, data from an M7 or M8 chip) of the individual, local environmental data (e.g., climate data, temperature data, light parameter data, etc.), nutrition or diet-related data (e.g., data from food establishment check-ins, data from spectrophotometric analysis, etc.) of the individual, biometric data (e.g., data recorded through sensors within the individual's mobile communication device, data recorded through a wearable or other peripheral device in communication with the individual's mobile communication device) of the individual, and any other suitable data. In examples, one or more of: a wireless-enabled scale, a blood pressure sensor, and a pulse-oximeter sensor can transmit the individual's weight, blood pressure, and blood oxygen level to a mobile communication device of the individual and/or a processing subsystem implementing portions of the method 100, and Block S120 can include receiving this data to further augment analyses performed in Block S140.

In relation to receiving data, Blocks S120 and/or S110 can additionally or alternatively include receiving data pertaining to individuals in contact with the individual during the period of time, such that data from the individual who experiences states of depression and data from others in communication with the individual are received (e.g., using information from an analogous application executing on the electronic device(s) of others in communication with the individual). As such, Blocks S120 and/or S110 can provide a holistic view that aggregates communication behavior data and contextual data of two sides of a communication involving the individual who experiences states of depression. In examples, such data can include one or more of: a second party's location during a phone call with the individual, the second party's phone number, the second party's length of acquaintance with the individual, and the second party's relationship to the individual (e.g., top contact, spouse, family member, friend, coworker, business associate, etc.).

Similar to Block S110, In relation to receiving the supplementary dataset, Block S120 can include transmitting the supplementary dataset from the mobile communication device S122 and/or any other suitable device or system that serves as a source of supplementary data, to the computing system, as shown in FIG. 2. In transmitting the supplementary dataset, one or more sensor modules (e.g., sensor module of the mobile communication device, sensor module of a wearable computing device, sensor of a biometric monitoring device, etc.) can transmit data to the computing system by way of a wired and/or wireless data link (e.g., over Bluetooth, over Bluetooth LTE, etc.). However, Block S120 can include another other suitable variation of transmitting supplementary data, and/or receiving supplementary data.

1.2 Method—Active Data

Block S130 recites: receiving a survey dataset including responses, to at least one of a set of depression-assessment surveys, associated with a set of time points of the time period, from the individual. Block S130 is preferably implemented at a module of the computing system described in relation to Blocks S110 and S120 above, but can additionally or alternatively be implemented at any other suitable system configured to receive survey data from one or more individuals. The survey dataset can include interview and/or self-reported information from the individual. Furthermore, the survey dataset preferably includes quantitative data, but can additionally or alternatively include qualitative data pertaining to a depressive state of the individual corresponding to at least a subset of the set of time points. Furthermore, while portions of the survey dataset preferably correspond to time points within the time period of Block S110, portions of the survey dataset can alternatively correspond to time points outside of the time period of Block S110 (e.g., as in a pre-screening or a post-screening survey). Additionally or alternatively, Block S130 can include receiving clinical data (e.g., information gathered in a clinic or laboratory setting by a clinician).

In Block S130, the set of time points can include uniformly or non-uniformly-spaced time points, and can be constrained within or extend beyond the time period of the log of use of the communication application of Block S110. As such, in variations, the set of time points can include regularly-spaced time points (e.g., time points spaced apart by an hour, by a day, by a week, by a month, etc.) with a suitable resolution for enabling detection of changes in a depressive state of the individual. Additionally or alternatively, provision of a survey and/or reception of responses to a survey can be triggered upon detection of an event of the individual (e.g., based upon data from sensors associated with the individual, based upon an output of an analysis of Block S140, etc.) or any other suitable change in state of the individual. Furthermore, for all time points of the set of time points, an identical subset of the set of depression-assessment surveys can be provided to the individual; however, in alternative variations, different subsets of the set of depression-assessment surveys can be provided to the individual at different time points of the set of time points.

In variations, the survey dataset can include responses to surveys configured to assess severity of depression in an individual along a spectrum, wherein the surveys transform qualitative information capturing an individual's affective state into quantitative data according to a response-scoring algorithm. In examples, the set of depression-assessment surveys can include surveys derived from one or more of: the Hamilton Rating Scale for Depression (HAM-D), with scores scaling from 0 (least severe) to 58 (most severe); the Patient Health Questionnaire (PHQ-9, PHQ-2) for screening, monitoring, and measuring depression severity according to Diagnostic and Statistical Manual (DSM) criteria for depression, with scores scaling from 0 (least severe) to 27 (most severe); the World Health Organization (WHO-5) quality of life assessment, with scores scaling from 0 (most severe) to 25 (least severe); the Patient Activation Measure (PAM) self-management assessment with levels scaling from 1 (most severe) to 4 (least severe); a demographic survey that receives demographic information of the patient; a medication adherence survey (for patients taking medication for depression); a mood/depression survey; and a recent care survey (e.g., covering questions regarding hospitalization and psychological care). However, the set of surveys can include any other suitable surveys (e.g., BDI, HDI, CES-D, PHQ-8, etc.) or adaptations thereof. As such, the survey dataset can include quantitative scores of the individual for one or more subsets of surveys for each of the set of time points (or a subset of the set of time points).

In relation to anxiety, which may or may not be comorbid with depression in the individual, the survey dataset can include responses to surveys configured to assess severity of anxiety in an individual along a spectrum, wherein the surveys transform qualitative information capturing an individual's state into quantitative data according to a response-scoring algorithm. In examples, surveys configured to assess states of anxiety can include surveys derived from one or more of: a general anxiety disorder (GAD) scale (e.g., a GAD-7 scale); a questionnaire for screening, monitoring, and measuring anxiety severity according to Diagnostic and Statistical Manual (DSM) criteria for anxiety; a daily assessment of symptoms—anxiety (DAS-A) questionnaire; a questionnaire for screening, monitoring, and measuring compulsive behavior severity according to Diagnostic and Statistical Manual (DSM) criteria for compulsive behavior; a Yale-Brown Obsessive Compulsive Scale (Y-BOCS); a questionnaire for screening, monitoring, and measuring panic attack severity according to Diagnostic and Statistical Manual (DSM) criteria for anticipatory attacks (DSM-IV-TR); a questionnaire for screening, monitoring, and measuring PTSD according to Diagnostic and Statistical Manual (DSM) criteria for PTSD; a Trauma Screening Questionnaire; a PTSD symptom scale; a social phobia inventory; a SPAT-B tool; a Liebowitz Social Anxiety Scale; a questionnaire for screening, monitoring, and measuring specific phobia severity according to Diagnostic and Statistical Manual (DSM) criteria for specific phobias (DSM-IV-TR); and any other suitable tool or survey.

In an example, the survey dataset comprises biweekly responses (e.g., for a period of 6 months) to the PHQ-9 survey, biweekly responses (e.g., for a period of 6 months) to the WHO-5 survey in alternation with the PHQ-9 survey, responses to the PAM assessment at an initial time point, at an intermediate time point (e.g., 1-month time point), and at a termination time point, responses to the HAM-D assessment at an initial time point and a termination time point, biweekly response to a recent care survey, daily responses to a mood survey, and twice-per-week responses to a medication adherence survey.

In some variations, Block S130 can further include facilitating automatic provision of at least one of the set of depression-assessment surveys at the mobile communication device(s) of the individual(s). As such, responses to one or more of the set of depression-assessment surveys can be provided by user input at an electronic device (e.g., a mobile communication device of the patient), or automatically detected from user activity (e.g., using suitable sensors). Additionally or alternatively, provision of at least one of the set of depression-assessment surveys can be performed manually by an entity (e.g., therapy providing entity, healthcare professional, relative, acquaintance, etc.) associated with an individual or received as derived from clinical data, with data generated from the survey(s) received in Block S130 by manual input. Additionally or alternatively, provision of at least one survey and/or reception of responses to the survey can be guided by way of an application executing at a device (e.g., mobile device, tablet) of a caretaker of the individual and/or the patient, wherein the application provides instruction (e.g., in an audio format, in a graphic format, in a text-based format, etc.) for providing the survey or the responses to the survey. Block S130 can, however, be implemented in any other suitable manner (e.g., by verbal communication over the phone, by verbal communication face-to-face, etc.).

Similar to Block S110, In relation to receiving the survey dataset, Block S130 can include transmitting the survey dataset from the mobile communication device S132 and/or any other suitable device or system that serves as a source of survey data, to the computing system, as shown in FIG. 2. In transmitting the survey dataset, one or more data storage modules (e.g., memory module of the mobile communication device, etc.) can transmit data to the computing system by way of a wired and/or wireless data link (e.g., over Bluetooth, over Bluetooth LTE, etc.). However, Block S130 can include another other suitable variation of transmitting survey data, and/or receiving survey data.

Blocks S110, S120, and S130 can thus provide passive data (e.g., unobtrusively collected data) and active data (e.g., survey data) that can be taken as inputs in Block S140 to generate analyses pertaining to present, past, and/or future depressive states of a patient.

1.3 Method—Modeling and Predicting Depression State

Block S140 recites: for at least a time point of the set of time points, transforming data from the log of use, the supplementary dataset, and the survey dataset into an analysis of a depression-risk state of the individual associated with at least a portion of the time period. Block S140 functions to determine values of one or more depression-risk parameters in association with at least one time point of the set of time points, based upon one or more of the log of use dataset, the supplementary dataset, and the survey dataset. Block S140 thus enables assessment of a past or current depressive state of the individual and/or predicts risk that the individual will trend toward a different (e.g., worsened, improved, etc.) depressive state at a future time point.

In the analysis, Block S140 can identify parameters/triggering events directly from passive data (i.e., the log of use dataset, the supplementary dataset) and/or from active data (i.e., the survey dataset), or can additionally or alternatively implement a predictive model that processes both passive and active components to predict one or more present or future depressive states of the individual, with training data. Additionally or alternatively, for individuals following a medication regimen for treatment or maintenance of health in relation to depression, the analyses of Block S140 can include generation of an adherence model that assesses or predicts adherence of the patient to the medication regimen as an output of the analysis.

1.3.1 Depression-Risk State—Predictive Model

Preferably, generating a predictive model S142 in association with Block S140 includes utilization of one or more machine learning techniques and training data (e.g., from the patient, from a population of patients), data mining, and/or statistical approaches to generate more accurate models pertaining to the patient's depression (e.g., over time, with aggregation of more data). As such, Block S142 is preferably implemented at a computing system configured to process data from the log of use dataset, the supplementary dataset, and the survey dataset. The computing system can be the same computing system associated with one or more of Blocks S110-S130 of the method 100, or can alternatively be any other suitable computing system.

In generating the predictive model, Block S142 preferably uses input data including communication behavior data from the log of use dataset, data from supplementary dataset, and data from the survey dataset to provide a set of feature vectors corresponding to time points of the time period. Feature selection approaches can include one or more of: factor analysis approaches that implement statistical methods to describe variability among observed features in terms of unobserved factors, in order to determine which features explain a high percentage of variation in data; correlation feature selection (CFS) methods, consistency methods, relief methods, information gain methods, symmetrical uncertainty methods, and any other suitable methods of feature selection. In variations, feature selection approaches can be implemented for any passive data (e.g., communication data, mobility data), wherein a linking analysis of Block S140 is then used to determine associations between features of passive data and states of disorder determined from active data (e.g., survey response datasets). Analysis of the passive data in relation to the active data, with regard to feature selection and associations between passive and active data can, however, be performed in any other suitable manner.

In one variation, the feature vectors can include features related to aggregate communication behavior, interaction diversity, mobility behavior (e.g., mobility radius as a measure of distance traveled by the individual within a given time period, such as the weekend), a number of missed calls, and a duration of time spent in a certain location (e.g., at home). In examples, feature vectors can be generated based upon aggregation of phone, text message, email, social networking, and/or other patient communication data for a particular period of time into one or more features for the patient for the particular time period. Furthermore, a feature can be specific to a day, a week, a month, a day period (e.g., morning, afternoon, evening, night), a time block during a day (e.g., one hour), a specific communication action (e.g., a single phone call, a set of communication actions of the same type (e.g., a set of phone calls within a two-hour period), all communications within a period of time, etc.). Additionally, combinations of features can be used in a feature vector. For example, one feature can include a weighted composite of the frequency, duration (i.e., length), timing (i.e., start and/or termination), and contact diversity of all outgoing voice (e.g., phone call) communications and a frequency, length, and timing and/or response time to (i.e., time to accept) incoming voice communications within the first period of time through a phone call application executing on the patient's mobile computing device. Feature vectors can additionally or alternatively include features based on analysis of voice communications, textual communications, mobile application activity usage, location data, and any other suitable data which can be based on variance, entropy, or other mathematical and probabilistic computations of basic data (e.g., a composite activity score, a composite socialization score, a work-life balance score, a quality-of-life score). However, the feature vectors can be determined in any other suitable manner.

In some variations, Block S142 can include utilizing statistics-based feature selection approaches to determine a subset of features from the log of use dataset, the supplementary dataset, and/or the survey dataset that have a high predictive power and/or high accuracy in generating one or more outputs of the predictive model. In examples, the statistical approaches can implement one or more of: correlation-based feature selection (CFS), minimum redundancy maximum relevance (mRMR), Relief-F, symmetrical uncertainty, information gain, decision tree analysis (alternating decision tree analysis, best-first decision tree analysis, decision stump tree analysis, functional tree analysis, C4.5 decision tree analysis, repeated incremental pruning analysis, logistic alternating decision tree analysis, logistic model tree analysis, nearest neighbor generalized exemplar analysis, association analysis, divide-and-conquer analysis, random tree analysis, decision-regression tree analysis with reduced error pruning, ripple down rule analysis, classification and regression tree analysis) to reduce questions from provided surveys to a subset of effective questions, and other statistical methods and statistic fitting techniques to select a subset of features having high efficacy from the data collected in Blocks S110, S120, and/or S130. Additionally or alternatively, any assessment of redundancy or efficacy in a feature derived from data of Blocks S110, S120, and/or S130 can be used to provide a measure of confidence in an output of the predictive model from one or more input features. Furthermore, the statistical approach(es) of Block S142 can be used to strategically reduce portions of data collected based upon redundancy and/or lack of utility of the data. Even further, the statistical approaches/feature selection approaches can be used to entirely omit collection of portions of the data (e.g., responses to specific surveys or portions of surveys can render responses to other portions of surveys or other surveys redundant), in order to streamline the data collection in Blocks S110, S120, and/or S130.

In one example, a high degree of correlation (e.g., positive correlation) between responses to a bi-weekly PHQ-9 assessment and a daily mood survey (e.g., a portion of recent responses to a daily mood survey in relation to a time point of interest, responses to the daily mood survey from 7 days before and 7 days after a session of responses to a PHQ-9 assessment) can be used to entirely omit provision of the bi-weekly PHQ-9 assessment or portions of the PHQ-9 assessment, in lieu of the daily mood survey, due to redundancy in data collection, in variations of the method 100. In another example, a high degree of correlation (e.g., positive correlation) between responses to a bi-weekly PHQ-9 assessment and mobility data from the supplementary dataset can be used to entirely omit provision of the bi-weekly PHQ-9 assessment or portions of the PHQ-9 assessment, in lieu of the mobility data, due to redundancy in data collection, in variations of the method 100. In still another example, a high degree of correlation (e.g., positive correlation) between a communication parameter derived from the log of use (e.g., call count predictability) and mobility data from the supplementary dataset can be used to entirely omit collection of data (e.g., call count data, mobility data) due to redundancy in data collection, in variations of the method 100. In still another example, a high degree of correlation (e.g., positive correlation) between a communication parameter derived from the log of use (e.g., predictability and entropy) and mobility data from the supplementary dataset can be used to entirely omit collection of data (e.g., call count data, mobility data) due to redundancy in data collection, in variations of the method 100.

In still other examples, correlations between active data and passive data including one or more of: positive correlations between daily mood survey score and call count/SMS count during peak hours, positive correlations between daily mood survey score and communication diversity, negative correlations between daily mood survey score and incoming call count during off-peak hours, negative correlations between daily mood survey score and SMS message length to a primary contact during peak hours, negative correlations between daily mood survey score and number of unreturned calls during off-peak hours, positive correlations between PHQ-9 assessment score and mobility, positive correlations between PHQ-9 assessment score and mobility radius, and negative correlations between PHQ-9 assessment score and call count predictability can be used to streamline data collection associated with Blocks S110, S120, and/or S130. However, any other suitable data derived from Blocks S110, S120, and S130 can be used to increase efficacy of data collection and/or determination of values of the depression-risk parameter in Block S142. Additionally or alternatively, any assessment of redundancy or efficacy in a feature derived from data of Blocks S110, S120, and/or S130 can be used to provide a measure of confidence in outputs of the predictive model determined from the feature(s).

In some embodiments, the predictive model generated in Block S142 can process a set of feature vectors according to methods described in relation to the predictive modeling engine described in U.S. application Ser. No. 13/969,339, entitled "Method for Modeling Behavior and Health Changes" and filed on 16 Aug. 2014, which is incorporated herein in its entirety by this reference; however, the predictive model can alternatively be generated in any other suitable manner. As such, in variations of the model(s), a set of feature vectors from the input data can be processed according to a machine learning technique (e.g., support vector machine with a training dataset) to generate the value(s) of the criticality parameter in association with a time point. In one example, the predictive model can incorporate historical data from the patient (e.g., survey responses from a prior week, a history of passive data from the log of use, etc.), with more weight placed upon more recent data from Blocks S110-S130 in determination of a depression-risk state associated with a time point by the predictive model; however, the predictive model can be implemented in any other suitable manner.

Furthermore, in extensions of the method 100 to a population of patients, the predictive model can be used to identify differences in passive data and/or active data, as associated with identified depression-risk states, between different demographics of individuals. For instance, the predictive model can be used to identify sets of feature vectors and/or subsets of features (e.g., related to communication behavior, related to survey responses, related to mobility behavior, etc.) that have high efficacy in determining risk/severity for one or more of: different genders, different age groups, different employment statuses, different ethnicities, different nationalities, different socioeconomic classes, and any other suitable demographic difference.

While some variations of machine learning techniques are described above, in relation to generation of the predictive model, Block S140 can additionally or alternatively utilize any other suitable machine learning algorithms. In variations, the machine learning algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the machine learning algorithm can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked auto-encoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm.

1.3.2 Depression-Risk State—Adherence Model

For patients taking medication to manage their depression, Block S140 can additionally or alternatively include processing datasets associated with Blocks S110, S120, and/or S130 with an adherence model S143 configured to assess and/or predict a state of adherence to a medication regimen by a patient. The adherence model can be an embodiment, variation, or example of an adherence model as described in U.S. application Ser. No. 13/969,339, entitled "Method for Modeling behavior and Health Changes", but can alternatively be any other suitable adherence model.

1.3.3 Depression-Risk State—Parameters of Analysis and Criticality Assessment

Figure 3:
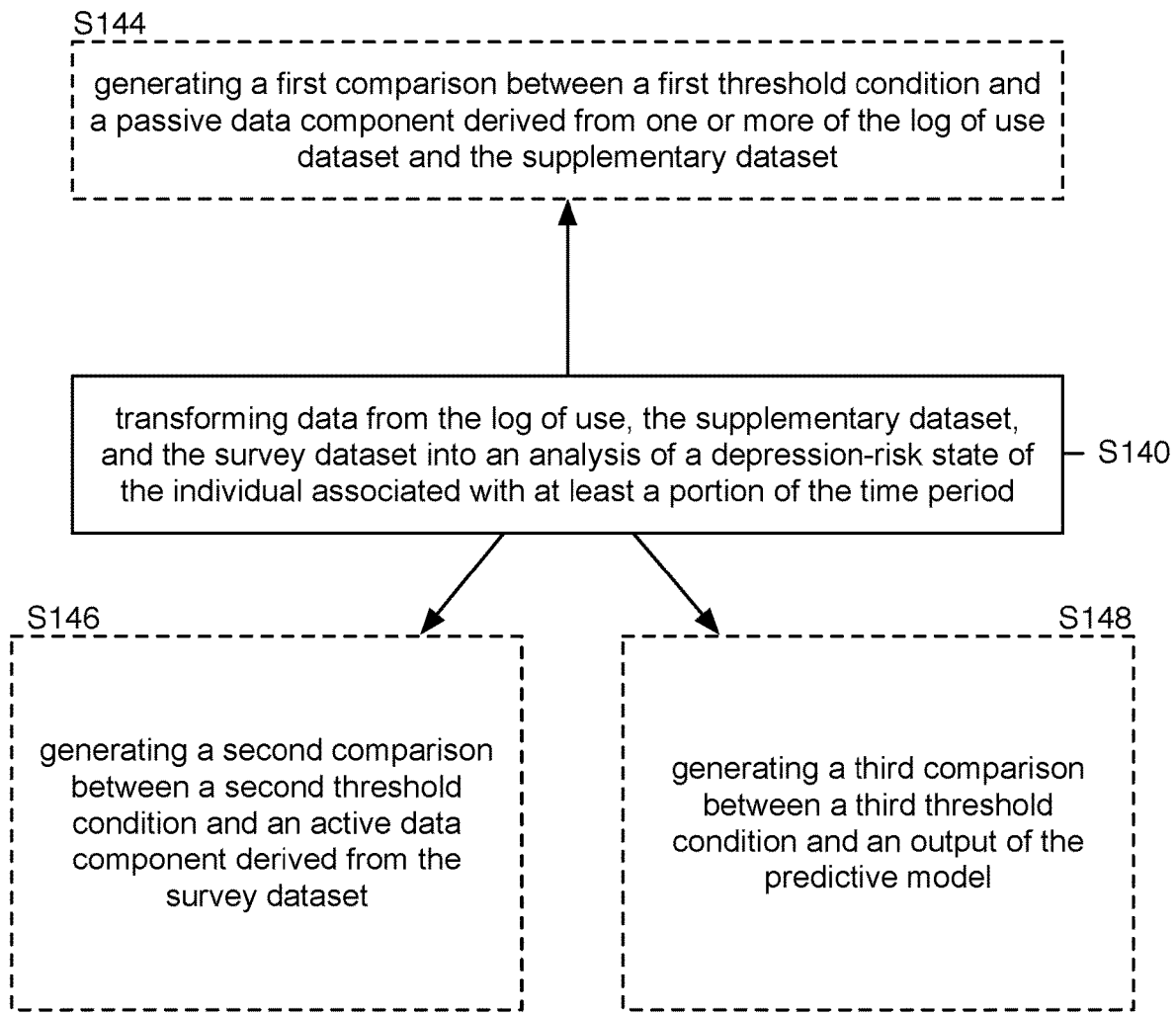
FIG. 3 is a flowchart of a variation of a portion of a method for modeling behavior and depression state.

In generating the analysis of a depression-risk state of the individual, Block S140 can include generating comparisons between different threshold conditions and one or more of: components of the log of use dataset, components of the supplementary dataset, components of the survey dataset and outputs of the predictive model. As such, generating the analysis of the depression-risk state of the individual in Block S140 can include one or more of: generating a first comparison between a first threshold condition and a passive data component derived from one or more of the log of use dataset and the supplementary dataset S144; generating a second comparison between a second threshold condition and an active data component derived from the survey dataset S146; and generating a third comparison between a third threshold condition and an output of the predictive model S148, as shown in FIG. 3. The comparisons of Blocks S144, S146, and/or S148 can thus be associated with parameters of the depression-risk state of the individual used to assess criticality of the depression state of the individual, and/or to resolve a critical depression state of the individual in subsequent blocks of the method 100.

Figure 4:
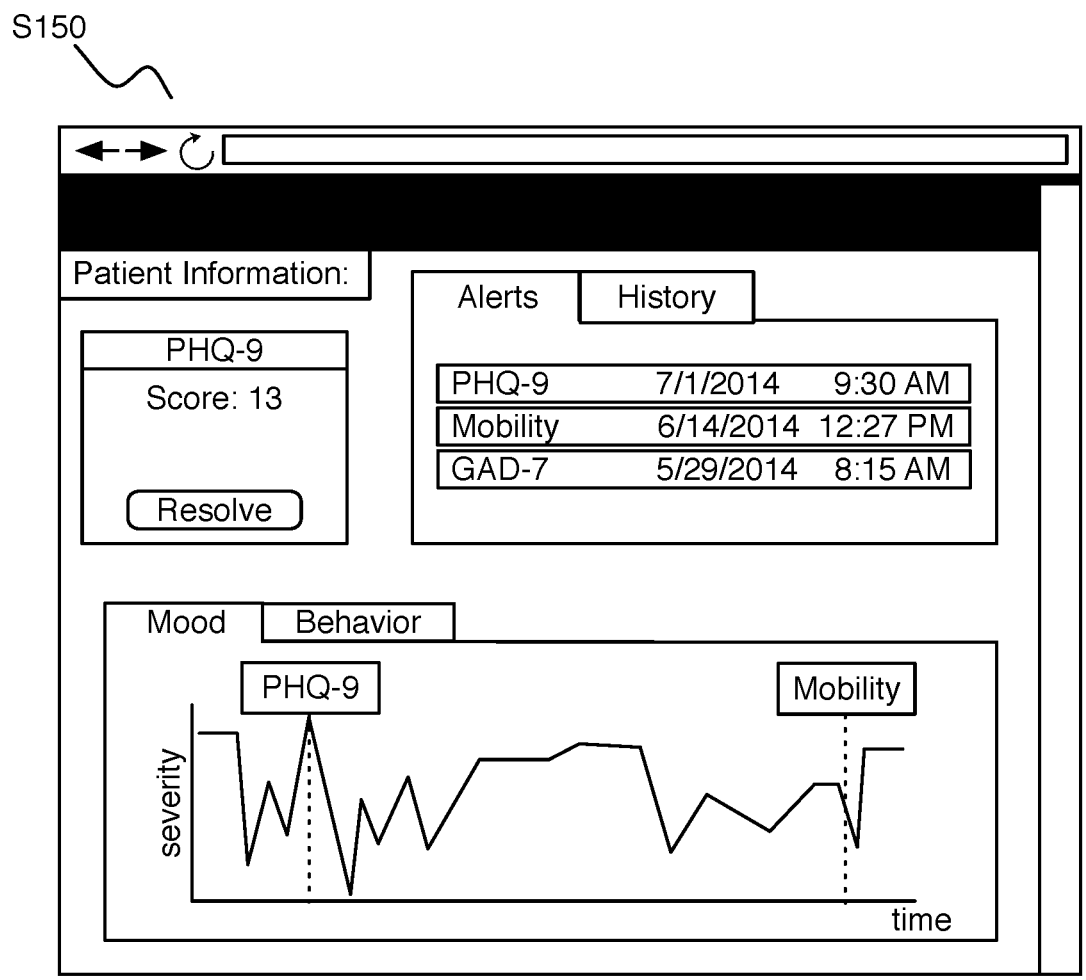
FIG. 4 depicts an example of a dashboard for providing an alert in an embodiment of a method for modeling behavior and depression state.

Blocks S144, S146, and S148 thus function to process the outputs of Blocks S110-S130 of the method 100, such that the resolution actions of Block S150 are derived from at least one of an active component (i.e., a component derived from the survey response dataset), a passive component (e.g., a clinically-informed behavioral rule component determined by heuristics), and a component derived from the predictive model generated in Block S142. In particular, consideration of the active component, the passive component, and the component derived from the predictive model can significantly strengthen the efficacy of the resolution actions implemented in Block S150, as shown in FIG. 4. Furthermore, each of the active component, the passive component, and the predictive model component can have an associated time frame that is identical or different to time frames of analysis of the other components. Additionally, analysis of each of the active component, the passive component, and the predictive model component can occur within one or more time frames that are different from the time frame of an associated resolution action.

Block S144 recites: generating a first comparison between a first threshold condition and a passive data component derived from one or more of the log of use dataset and the supplementary dataset. In Block S144, generating the first threshold condition and a passive data element can comprise defining one or more categories of passive behaviors of the individual (e.g., related to lethargy, related to social isolation, related to physical isolation, related to evolution of the patient's support network, related to time spent at work, related to weekly behavioral patterns, etc.) based upon historical behavior of a patient within a duration of time (e.g., immediately prior 4-6 weeks of the individual's life). Then, Block S144 can include comparing the features of or evolution in the passive behavior(s) of the individual to the first threshold condition. In variations wherein the passive behaviors of the patient are monitored for a duration of time, the first threshold condition can additionally or alternatively include a frequency threshold and/or a frequency-within-a-duration-of-time threshold, in relation to generation of an indication based upon a passive data component.

In variations, the first threshold condition can include one or more of: a threshold condition of a mobility less than the loth percentile of values of a mobility-related parameter (e.g., mobility radius) for the time period (e.g., a time window of 60 days, including 30 values of the mobility-related parameter); a threshold condition of a mobility less than the $25^{th}$ percentile of values of a mobility-related parameter (e.g., mobility radius) for the time period (e.g., a time window of 60 days, including 30 values of the mobility-related parameter); a threshold condition of a set of values of a mobility-related parameter having low values for a number of consecutive days; a threshold condition of a number of unreturned calls greater than 5 for a number of consecutive days; a threshold condition of a number of unreturned calls greater than 3 for a number of consecutive days; a threshold condition of a duration of time spent at home having a value greater than 22 hours per day for a number of consecutive days; a threshold condition of a duration of time spent at home having a value greater than 22 hours per day for a number of consecutive days; a threshold condition of communication behavior greater than the top $15^{th}$ percentile of values of communication-related parameter (e.g., communication count) for a number of consecutive days within a time period (e.g., a time window of 60 days, including 30 values of the communication-related parameter); a threshold condition of communication behavior less than the bottom $30^{th}$ percentile of values of communication-related parameter (e.g., communication diversity) for a number of consecutive days within a time period (e.g., a time window of 60 days, including 30 values of the communication-related parameter); any other suitable threshold condition; and any other suitable combination of threshold conditions.

In examples, the first comparison can thus facilitate identification of one or more of: a period of lethargy exhibited as a persistent reduction in mobility (e.g., little motion over a period of 3 consecutive days); a period of social isolation exhibited as persistence in unreturned communications (e.g., a period of 3 days of unreturned phone calls, a period of 3 days of unreturned text-based communications, etc.); a period of physical isolation exhibited as persistence in staying in a location (e.g., staying primarily at the same location for a period of 3 or more days); a reduction in the individual's support network exhibited as communicating with fewer people than typical for the patient; a combination of multiple passive behaviors that satisfy a threshold condition (e.g., two passive behaviors that meet a threshold within 3 days); and any other suitable condition for indication generation.

Block S146 recites: generating a second comparison between a second threshold condition and an active data component derived from the survey dataset. In Block S146, generating the second comparison between the second threshold condition and the active component derived from the survey response dataset can comprise assigning a score to one or more elements of the survey response dataset for a patient (e.g., based upon one instance of survey response provision, based upon multiple instances of survey response provision), and comparing the score(s) to the second threshold condition. In variations wherein the survey response dataset comprises responses to survey questions (e.g., a repeat set of survey questions) at each of a set of time points, the second threshold condition can additionally or alternatively include a frequency threshold and/or a frequency-within-a-duration-of-time threshold, in relation to generation of an indication based upon an active component. Furthermore, threshold conditions can be defined in relation to a baseline for each patient, based upon historical behavior of the individual.

As such, in variations, the second comparison can indicate one or more of: a score greater than a given threshold; a score greater than a given threshold for a certain duration of time; a change in score greater than a given threshold; a change in score greater than a given threshold as derived from the patient's historical score data; and any other suitable comparison. Furthermore, the comparison(s) can additionally or alternatively be generated based upon a percentile condition, a standard deviation (e.g., in score) condition, outlier detection analysis (e.g., of a score in relation to scores from the individual), and/or any other suitable condition, based upon analysis of a patient in isolation, based upon analysis of the individual's recent behavior in isolation, based upon analysis of a population of individuals, and/or any other suitable grouping of individuals.

In examples, the second comparison can facilitate identification of one or more of: a score for survey responses that surpasses a critical threshold score (e.g., a score above a critical value on a PHQ-9 survey); a change in survey score that surpasses a critical threshold; a set of scores for survey responses acquired at each of a set of time points within a duration of time, wherein a threshold proportion of the set of scores surpasses a critical threshold score (e.g., 2 of 3 surveys have scores above a critical threshold); a summation of scores for a set of scores for survey responses acquired at each of a set of time points that surpasses a critical threshold; a magnitude of difference in scores for survey responses acquired at different time points that surpasses a critical threshold (e.g., a PHQ-9 score >15, which is greater than a previous score); a combination of scores for different surveys that surpasses a critical threshold for each of the different surveys; and any other suitable condition for indication generation.

Block S148 recites: generating a third comparison between a third threshold condition and an output of the predictive model. In Block S150, generating the third comparison between the third threshold condition and the output of the predictive model can comprise identification of a classification (e.g., a learned, complex, non-intuitive, and/or behavioral association exhibited by the individual), and comparing the classification to a threshold condition. In variations, a single feature and/or combinations of features derived from the log of use dataset, the supplementary dataset, and, the survey response dataset (e.g., with weighting among factors) can be compared to one or more threshold conditions, in identifying if an alert based upon the predictive model of Block S142 should be generated. In variations and examples, the third comparison can be generated as described in U.S. application Ser. No. 13/969,339, entitled "Method for Modeling behavior and Health Changes" and filed on 16 Aug. 2014.

As such, in one example of Blocks S144, S146, and S148, accounting for a passive component, an active component, and a predictive model component, an indication can be based upon: a first passive component (e.g., related to communication behavior) generated from a first 3-day window of time, a second passive behavioral component (e.g., related to mobility of the individual) generated from a second window of time overlapping with the first 3-day window of time, scoring of a biweekly survey, and a predictive model component for a time window of 14 days (e.g., overlapping with the period of the biweekly survey), wherein the predictive model component implements an aggregated learning approach based upon multiple individual models (e.g., each assessing different parameters and/or different time periods of patient behavior).

The analyses of Block S140 can, however, include generation of any other suitable comparison and/or any other suitable output which serve as parameters of the depression-risk state of the individual. Additionally or alternatively, the comparison(s) generated in Blocks S144, S146, and S148 can include identification or analysis of patient progress through a condition (e.g., in relation to persistence of symptoms, in relation to worsening of symptoms, in relation to improvement of symptoms, etc.).

1.4 Method—Resolution of Critical States of Depression

Block S150 recites: generating an alert based upon one or more outputs of the analysis of Block S140, which functions to provide an indication that the individual is experiencing a critical state of depression and/or is trending toward a critical state of depression. Block S150 can thus include generating an alert upon detection, at the computing system performing the analysis, that one or more outputs (e.g., comparisons) from the analysis of the depression-risk state satisfy associated threshold conditions. The alert of Block S150 can be an alert that prompts transmission of a notification to an entity associated with the individual, for instance, for therapeutic intervention. The alert can additionally or alternatively comprise an alert that serves as an input into a subsequent computer-implemented module for automatically providing an intervention to the individual, the intervention intended to improve the depression-related state of the individual.

As such, Block S150 can include Block S152, which recites: transmitting an alert based upon the analysis. Block S152 functions to alert at least one of an entity associated with the individual and/or the individual regarding a critical state of depression that the patient has or will enter. Thus, Block S152 can provide an alert to an entity at a critical time point at which the alert has an increased or optimal effectiveness in preventing a regression in depression-state of the patient. The alert can be a visual alert (e.g., text-based alert, graphic alert), audio alert, haptic alert, and/or any other suitable type of alert. In relation to an entity associated with the patient(s), the entity can include any one or more of: a caretaker, a healthcare provider, a relative (e.g., parent, significant other, etc.), and any other suitable entity associated with the patient. Furthermore, in relation to an entity associated with the patient(s), the alert(s) can be provided at a dashboard of an electronic interface (e.g., web portal, computing device, etc.) accessible by the entity. In the example shown in FIG. 4, alert(s) of Block S152 can be provided at a dashboard of a web portal, wherein the alert(s) are text-based alerts including a type of alert (e.g., related to active data, related to passive data), a value of a depression-risk parameter associated with the alert, and a graphic that displays values of one or more scores of a survey (e.g., a daily mood survey) and/or a depression-risk parameter over time. In the example, the graphic can include tags that facilitate identification of associations between metrics derived from active components and passive components (e.g., mobility parameter values in association with scores on a PHQ-9 assessment and/or scores on a daily mood survey). The dashboard can further provide an option to resolve the alert, wherein in examples, resolution of the alert can include any one or more of: triaging an individual's depressive state, providing emotional support to the individual to improve the patient's depressive state, assessing the level of follow up care needed to improve the individual's state (e.g., by facilitating an appointment with a primary care physician within 3 days, by alerting a friend of the patient, by facilitating immediate transfer of the individual to an emergency room, etc.), by providing a short term plan to the patient to improve the patient's depressive state in an acute manner, by providing a long term plan to the individual that is configured to maintain a healthy state of the patient, and any other suitable resolving act (e.g., storing information/data resulting from a resolution action for future reference).

In relation to the comparison(s) of Blocks S144, S146, and S148, the alert can comprise an alert associated with active data (e.g., alerts related to PHQ-9 scores, alerts related to PHQ-2 scores, alerts related to daily mood scores, alerts related to medication adherence, etc.). Additionally or alternatively, the alert can comprise an alert associated with passive data (e.g., alerts related to lethargy associated with a mobility parameter, alerts related to social isolation in association with unreturned calls, alerts related to physical isolation in association with time spent at a location alone, alerts associated with reaching out to a support network associated with number of communication counts, alerts associated with reaching out to a support network associated with communication diversity, etc.). However, in variations of the specific examples noted above, the alerts can be associated with any other suitable form of active/passive data derived from other blocks of the method 100. As such, the alert can comprise any other suitable alert configured to facilitate improvement of the depressive state of the patient.

Figure 5A:
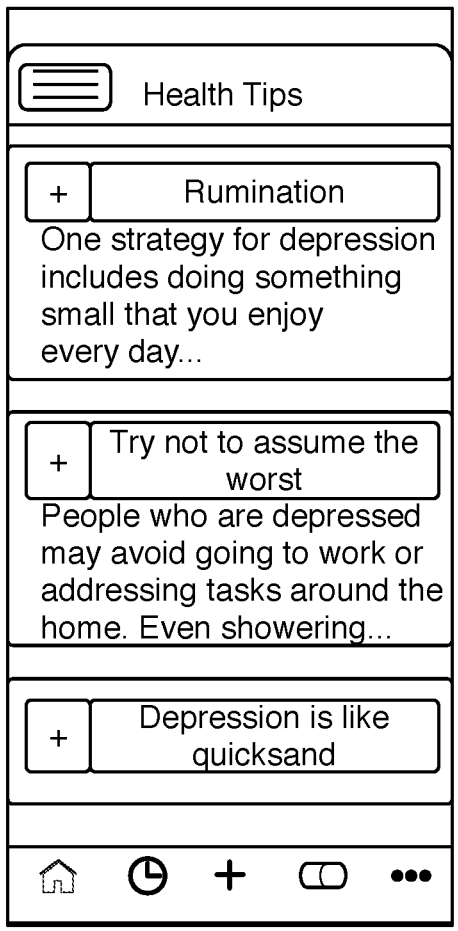
FIGS. 5A and 5B depict example notifications in an example of a method for modeling behavior and depression state.
Figure 5B:
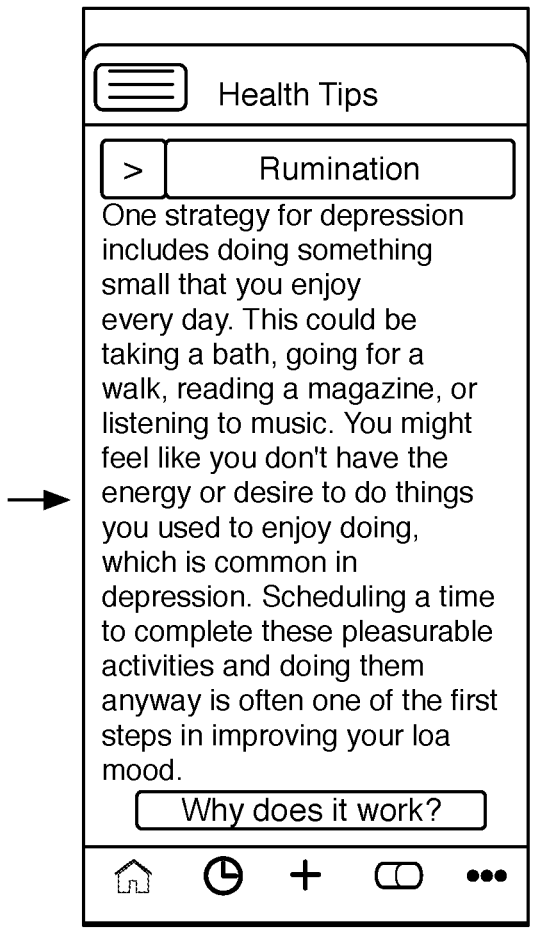

In some variations, as shown in FIG. 1, the method 100 can further include Block S160, which recites: providing a notification to the individual, at the mobile communication device, in response to the analysis. Block S160 functions to provide information, advice, and/or motivational content to the individual so that the patient can improve his/her depressive state, and/or maintain a healthy state. In variations of Block S160, the notifications can be provided with any suitable regular or non-regular frequency, can be provided with a sequence or in a random manner, can be triggered by an event, or can be provided in any other suitable manner. Furthermore, the notifications can include one or more of: a visual notification (e.g., text-based notification, graphic notification), an audio notification, a haptic notification, and any other suitable type of notification. In one example, a mobile communication device of a patient can download (e.g., upon initiation of download by one or more of the individual and an entity associated with the individual) and subsequently display the notification for the patient at a display of the mobile communication device, as shown in FIGS. 5A and 5B. The notifications can be personalized to the individual, or can be provided in the same manner to each of a population of individuals. In variations wherein the notifications are personalized to the individual, Block S160 can utilize a machine learning technique to identify the types of notifications that the patient responds positively to and/or negatively to, as assessed by patient outcomes in relation to depressive state (e.g., indicated in values of the depression-risk parameter).

In some variations, the notification can include one or more health improving tips and/or any other suitable therapeutic invention characterized by a therapy orientation (e.g., motivational, psychoeducational, cognitive behavioral, biological, physical, mindfulness-related, relaxation-related, dialectical behavioral, acceptance-related, commitment-related, etc.) and a category (e.g., pros and cons of change, depression-course and resolution, behavioral activation, insomnia, abdominal breathing, automatic thoughts, gratitude, mind wandering, cognitive distortions, exercise, rumination, facial feedback, diet, mindfulness, sleep inertia, compassion, social support, scheduling regularity, savoring, distress tolerance, positive evidence, rewards, sunlight exposure, muscle relaxation, assertiveness, supplements, avoidance, etc.) configured to address a variety of factors contributing to depression. As such, the notification can provide advice to combat depression and promote positive thinking based upon academic, clinical, and/or other forms of research. The notification can additionally or alternatively be provided as described in U.S. application Ser. No. 13/969,339, entitled "Method for Modeling Behavior and Health Changes", and/or in any other suitable manner.

In some variations, as shown in FIG. 1, the method 100 can further include Block S170, which recites: automatically initiating provision of a therapeutic intervention for the individual by way of at least one of the computing system and the mobile communication device. Block S170 functions to automatically and actively promote improvements to the individual's depressive state, and/or to facilitate maintenance of a healthy state in the individual. In some variations, automatically initiating provision of a therapeutic intervention can include generating a therapy regimen configured to improve the depressive state of the patient, based upon the analysis of Block S140. In associated variations, the therapy regimen can include therapeutic measures including any one or more of: psychiatric management measures (e.g., education of the patient, education of acquaintances of the patient, forming alliances, providing support groups, etc.), pharmacotherapeutic measures (e.g., antidepressant medications), psychotherapeutic measures (e.g., cognitive behavioral therapy, interpersonal therapy, problem solving therapy, psychodynamic psycotherapy), electroconvulsive therapeutic measures, and any other suitable therapeutic measure.

Furthermore, the therapy regimen and/or other therapeutic interventions can be provided using one or more of: healthcare provider interactions (e.g., therapeutic sessions with a counselor), pharmaceutical compound distributors, mobile application implemented methods, web browser-facilitated methods, and any other suitable avenue of therapy provision. The therapy regimen can additionally or alternatively be provided in a manner similar to that described in U.S. application Ser. No. 13/969,339, entitled "Method for Modeling Behavior and Health Changes", with therapy/treatment efficacy analyzed by a treatment regimen model and/or a treatment efficacy model. The therapy regimen can, however, be provided in any other suitable manner or assessed in any other suitable manner.

The method 100 can, however, include any other suitable blocks or steps configured to model behavior and depressive state, and/or improve a depressive state of a patient. Furthermore, as a person skilled in the art will recognize from the previous detailed description and from the figures and claims, modifications and changes can be made to the method 100 without departing from the scope of the method 100.

2. System

Figure 6:
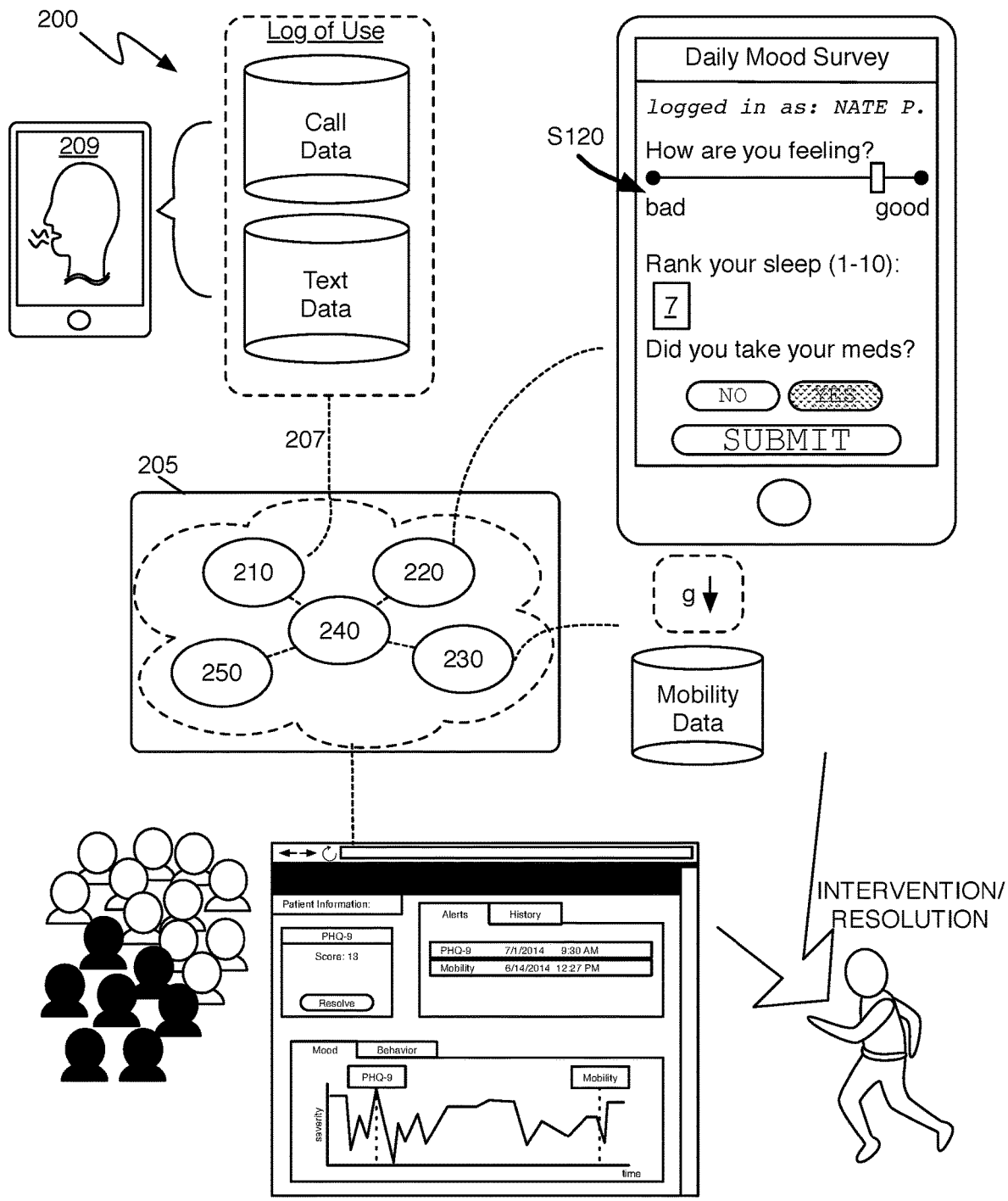
FIG. 6 depicts an embodiment of a system for modeling behavior and depression state.

As shown in FIG. 6, a system 200 for modeling behavior and depression state of a individual includes: a processing system 205 including: an interface 207 with a communication data aggregation module executing on a mobile communication device 209 of the patient; a first module 210 configured to access a log of use of a communication application coupled to the communication data aggregation module on the mobile communication device by the individual within a time period; a second module 220 configured to receive a supplementary dataset characterizing activity of the patient in association with the time period; a third module 230 configured to receive a survey dataset including responses, to at least one of a set of depression-assessment surveys, associated with a set of time points of the time period, from the patient; a fourth module 240 configured to transform data from the log of use, the survey dataset, and the supplementary dataset into an analysis of a depression-risk state of the individual; and a fifth module 250 configured to generate an alert based upon one or more outputs of the analysis.

The system 200 functions to perform at least a portion of the method 100 described in Section 1 above, but can additionally or alternatively be configured to perform any other suitable method for modeling behavior and depression of a patient. The system 200 is preferably configured to facilitate reception and processing of a combination of active data (e.g., survey responses) and passive data (e.g., unobtrusively collected communication behavior data, mobility data, etc.), but can additionally or alternatively be configured to receive and/or process any other suitable type of data. As such, the processing system 205 can be implemented on one or more computing systems including one or more of: a cloud-based computing system (e.g., Amazon EC3), a mainframe computing system, a grid-computing system, and any other suitable computing system. Furthermore, reception of data by the processing system 205 can occur over a wired connection and/or wirelessly (e.g., over the Internet, directly from a natively application executing on an electronic device of the patient, indirectly from a remote database receiving data from a device of the patient, etc.).

The processing system 205 and data handling by the modules of the processing system 205 are preferably adherent to health-related privacy laws (e.g., HIPAA), and are preferably configured to privatize and/or anonymize patient data according to encryption protocols. In an example, when an individual installs and/or authorizes collection and transmission of personal communication data by the system 200 through the native data collection application, the application can prompt the individual to create a profile or account. In the example, the account can be stored locally on the individual's mobile communication device 209 and/or remotely. Furthermore, data processed or produced by modules of the system 200 can be configured to facilitate storage of data locally (e.g., on the individual's mobile communication device, in a remote database), or in any other suitable manner. For example, private health-related patient data can be stored temporarily on the individual's mobile communication device in a locked and encrypted file folder on integrated or removable memory. In this example, the individual's data can be encrypted and uploaded to the remote database once a secure Internet connection is established. However, data can be stored on any other local device or remote data in any other suitable way and transmitted between the two over any other connection via any other suitable communication and/or encryption protocol. As such, the modules of the system 200 can be configured to perform embodiments, variations, and examples of the method 100 described above, in a manner that adheres to privacy-related health regulations.

The method 100 and/or system 200 of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for improving depression state determination and monitoring for a user, the method comprising:
receiving a first communication dataset from an application executing on a mobile communication device of the user, wherein the first communication dataset comprises a first set of message transcripts associated with a first time period;
with a first model, deriving a first textual content associated with the first set of message transcripts;
with a second model, wherein the second model comprises a trained predictive model, determining a first set of depression risk parameters associated with the user based on the first textual content;

assessing the first set of depression risk parameters to determine a first depression risk state associated with the user;

in response to and based on the first depression risk state, determining and initiating provision of a first therapeutic intervention at the mobile communication device, the first therapeutic intervention operable to improve the depression state of the user;

receiving a second communication dataset from the application, wherein the second communication dataset comprises a second set of message transcripts associated with a second time period, the second time period occurring later in time than the first time period;

with the first model, deriving a second textual content associated with the second set of message transcripts;

with the second model, determining a second depression risk state associated with the user based on the second textual content;

in response to the second depression risk state and based on a change from the first depression risk state to the second depression risk state, determining and initiating provision of a second therapeutic intervention at the mobile communication device, the second therapeutic intervention operable to improve the depression state of the user;

updating the second model based on the change from the first depression risk state to the second depression risk state, wherein updating the second model is operable to increase a predictive accuracy of the second model for the user; and with the updated second model, determining a third depression risk state associated with the user based on a third textual content.

2. The method of claim 1, wherein the first model is a trained model.

3. The method of claim 1, wherein the textual content comprises a set of content features, the set of content features indicative of at least one of a set of negative sentiments and a set of positive sentiments associated with the set of message transcripts.

4. The method of claim 1, further comprising, with the first model, determining a set of temporal parameters associated with the first communication dataset, wherein the first set of depression risk parameters is further determined based on the set of temporal parameters.

5. The method of claim 4, wherein the set of temporal parameters comprises at least one of: a frequency associated with receipt of message transcripts of the first set of message transcripts; and a time associated with receipt of message transcripts of the first set of message transcripts.

6. The method of claim 1, further comprising, with the first model, determining a set of message lengths associated with message transcripts of the first set of messages, wherein the set of depression risk parameters is further determined based on the set of message lengths.

7. The method of claim 1, wherein assessing the first set of depression risk parameters to determine the first depression risk state comprises comparing the first set of depression risk parameters with a set of thresholds.

8. A method for improving depression state determination and monitoring for a user, the method comprising:

receiving a first communication dataset from an application executing on a mobile communication device of the user;

with a trained predictive model, determining a first set of depression risk parameters associated with the user based on the first communication dataset;

assessing the first set of depression risk parameters to determine a first depression risk state associated with the user;

in response to and based on the first depression risk state, determining and initiating provision of a first therapeutic intervention at the mobile communication device, the first therapeutic intervention operable to improve the depression state of the user;

receiving a second communication dataset from the application, wherein the second communication dataset is associated with a second time period, the second time period occurring later in time than the first time period;

with the trained predictive model, determining a second depression risk state associated with the user based on the second communication dataset;

in response to and based on the second depression risk state, determining and initiating provision of a second therapeutic intervention at the mobile communication device, the second therapeutic intervention operable to improve the depression state of the user; and updating the trained predictive model based on the second depression risk state wherein updating the trained predictive model is operable to increase a predictive accuracy of the trained predictive model to determine a depression risk state associated with the user; and with the updated trained predictive model, determining a third depression risk state associated with the user based on a third communication dataset.

9. The method of claim 8, wherein the first communication dataset comprises a first set of message transcripts and wherein the second communication dataset comprises a second set of message transcripts.

10. The method of claim 9, further comprising:

determining a first textual content associated with the first set of message transcripts, wherein the first set of depression risk parameters is determined based on the first textual content; and determining a second textual content associated with the second set of message transcripts, wherein the second set of depression risk parameters is determined based on the second textual content.

11. The method of claim 10, wherein each of the first and second textual contents is associated with at least one of a positive and negative sentiment.

12. The method of claim 8, further comprising determining a change from the first depression risk state to the second depression risk state, wherein the trained predictive model is updated based on the change.

13. The method of claim 12, further comprising receiving a survey dataset from the user during the second time period, wherein the second depression risk state is further determined based on the survey dataset.

14. The method of claim 8, further comprising determining a set of features associated with the user, wherein the trained predictive model is determined based on the set of features.

15. The method of claim 14, wherein the trained predictive model is further determined based on aggregated data from a set of multiple users, wherein the set of multiple users share one or more of the set of features with the user.

16. The method of claim 8, further comprising determining a set of temporal parameters associated with the first communication dataset, wherein the first set of depression risk parameters is further determined based on the set of temporal parameters.

17. The method of claim 16, wherein the set of temporal parameters comprises at least one of: a frequency associated with receipt of a set of messages of the first communication dataset; and a time associated with receipt of the set of messages.

18. The method of claim 8, wherein assessing the first set of depression risk parameters to determine the first depression risk state comprises comparing the first set of depression risk parameters with a set of thresholds.

* * * * *

UNITED STATES PATENT AND TRADEMARK OFFICE
CERTIFICATE OF CORRECTION

PATENT NO. : 11,908,585 B2
APPLICATION NO. : 17/517561
DATED : February 20, 2024
INVENTOR(S) : Sai Moturu et al.

It is certified that error appears in the above-identified patent and that said Letters Patent is hereby corrected as shown below:

In the Claims

Column 22, Line 22, In Claim 8, after "state", insert --,--

Signed and Sealed this
Second Day of April, 2024

Katherine Kelly Vidal
*Director of the United States Patent and Trademark Office*